(12) United States Patent
Krammer et al.

(10) Patent No.: US 6,237,178 B1
(45) Date of Patent: May 29, 2001

(54) TOOTHBRUSH COMPRISING A BRUSH MEMBER HAVING BRISTLES OF DIFFERENT LENGTHS, AND BRUSH MEMBER HAVING BRISTLES OF DIFFERENT LENGTHS FOR A TOOTH BRUSH

(75) Inventors: Michael Krammer, Graz; Dieter Sturm, Klagenfurt, both of (AT)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 08/988,592

(22) Filed: Dec. 11, 1997

(30) Foreign Application Priority Data

Dec. 17, 1996 (EP) ................................................. 96890194

(51) Int. Cl.$^7$ .................................................. A46B 13/02
(52) U.S. Cl. ............................. 15/22.1; 15/28; 15/DIG. 5
(58) Field of Search .............................. 15/28, 22.4, 22.2, 15/22.1, 29, DIG. 5

(56) References Cited

U.S. PATENT DOCUMENTS

| | | | |
|---|---|---|---|
| 3,242,516 | * | 3/1966 | Cantor ........................................ 15/28 |
| 3,978,852 | * | 9/1976 | Annoni ...................................... 15/22.2 |
| 4,399,582 | | 8/1983 | Ernest et al. ............................. 15/176 |
| 5,276,932 | * | 1/1994 | Byrd ........................................... 15/28 |
| 5,461,744 | * | 10/1995 | Merbach ................................. 15/22.1 |
| 5,732,433 | * | 3/1998 | Gocking et al. ....................... 15/22.1 |
| 5,862,559 | * | 1/1999 | Hunter ..................................... 15/28 |
| 5,867,856 | * | 2/1999 | Herzog .................................... 15/28 |
| 5,974,615 | * | 11/1999 | Schwarz-Hartmann et al. ........ 15/28 |

FOREIGN PATENT DOCUMENTS

| | | |
|---|---|---|
| 4309035A1 | 9/1994 | (DE) . |
| 4438731A1 | 5/1996 | (DE) . |

* cited by examiner

Primary Examiner—Gary K. Graham
(74) Attorney, Agent, or Firm—Ernestine C. Bartlett

(57) ABSTRACT

Toothbrush comprising a brush member having bristles of different lengths, and brush member having bristles of different lengths for a tooth brush. In a toothbrush (1) comprising a grip member (2) and a brush member (36) connected to the grip member (2), which brush member has a longitudinal axis (39) and carries a bristle holder (40) which is mounted on the brush member (36) so as to be movable with respect to a holder axis (41) and which has a holder surface (69) which extends substantially transversely to the holder axis (41) and from which, in the area of the holder surface (69), bristles (70) project transversely to the holder surface (69) and together form a bristle field (71), the free ends of at least a part of the bristles (70) of the bristle field (71) arranged around the holder axis (41) are bounded by two non-stepped enveloping surfaces (72, 73) which are inclined continuously with respect to the bristle holder (40), which enveloping surfaces are arranged substantially in a V-shape relative to the holder surface (69) of the bristle holder (40) and intersect one another along a line of intersection (74) at the location of the holder axis (41), the line of intersection (74) of the two enveloping surfaces (72, 73) extending transversely to the longitudinal axis (39) of the brush member (36).

26 Claims, 3 Drawing Sheets

TOOTHBRUSH COMPRISING A BRUSH MEMBER HAVING BRISTLES OF DIFFERENT LENGTHS, AND BRUSH MEMBER HAVING BRISTLES OF DIFFERENT LENGTHS FOR A TOOTH BRUSH

BACKGROUND OF THE INVENTION

The invention relates to a toothbrush comprising a grip member and a brush member connected to the grip member, which brush member has a longitudinal axis and whose end remote from the grip member carries a bristle holder which is movable beyond a center position, which bristle holder is mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, which bristles together form a bristle field and are arranged around the holder axis and of which the peripheral bristles situated at the periphery of the bristle field are longer than the bristles situated in the inner part of the bristle field.

The invention further relates to a brush member for a toothbrush, which brush member can be coupled detachably to a grip member of the toothbrush, which brush member has a longitudinal axis and at one end carries a bristle holder which is movable beyond a center position, which bristle holder is mounted on the brush member so as to be movable with respect to a holder axis which extends transversely to the longitudinal axis and which bristle holder has a holder surface which extends substantially transversely to the holder axis and from which, in the area of the holder surface, bristles project transversely to the holder surface, which bristles together form a bristle field and are arranged around the holder axis and of which the peripheral bristles situated at the periphery of the bristle field are longer than the bristles situated in the inner part of the bristle field.

Such a toothbrush of the type defined in the first paragraph and such a brush member of the type defined in the second paragraph are known, for example from the document DE 43 09 035 A1. This known toothbrush and this known brush member comprise a substantially circular disc-shaped bristle holder carrying a bristle field which can be enveloped by a tangential surface formed by a cylindrical surface. The bristle filed comprises tufts of bristles arranged in an outer ring, the bristles of all the tufts arranged in the outer ring have the same length. Inside the outer ring of tufts further tufts of bristles are disposed, of which all the bristles also have the same length but the length of the bristles of the inner tufts being smaller than the length of the bristles of the tufts disposed in the outer ring. Owing to the bristle field configuration described above, in which there is a stepped transition between the tufts in the outer ring and the tufts inside the bristle field, comparatively good cleaning results are attainable with the known toothbrush and the known brush member, but tests have revealed that in many cases the cleaning results are not wholly satisfactory.

SUMMARY OF THE INVENTION

It is an object of the invention to further improve a toothbrush of the type defined in the first paragraph and a brush member of the type defined in the second paragraph and to obtain a higher cleaning performance and improved cleaning results.

According to the invention, in order to achieve this object in a toothbrush of the type defined in the first paragraph, the free ends of at least a part of the bristles of the bristle field arranged around the holder axis are bounded by two non-stepped enveloping surfaces which are inclined continuously with respect to the holder surface of the bristle holder, which enveloping surfaces are arranged substantially in a V-shape and intersect one another along a line of intersection at the location of the holder axis, and the line of intersection of the two enveloping surfaces extends transversely to the longitudinal axis of the brush member. Thus, it is achieved that the variation in level of the free ends of the bristles of the bristle field of a toothbrush in accordance with the invention can be without steps and the free ends of the bristles can be formed so as to be situated at a continuously varying level and the continuous variation in level of the free ends of the bristles of the bristle field is essentially mirror-symmetrical with respect to the holder axis and the line of intersection of the two enveloping surfaces, which line extends transversely to the longitudinal axis of the brush member. This has proved to be favorable for a correct positioning of the bristle field with respect to the curved tooth surfaces, which surfaces are essentially mirror-symmetrical relative to a surface tangent which is also oriented transversely to the longitudinal axis of the brush member, and consequently for a satisfactory cleaning action of the bristles of the bristle field. Furthermore, it is to be noted that a construction in accordance with the invention has also proved to be advantageous in view of a simple implementation of the level variation of the bristle ends, i.e. of the bristle field topography.

It is to be noted that from the document U.S. Pat. No. 4,399,582 A a toothbrush in several variants is known, including one variant comprising a bristle holder and a bristle field arranged on this bristle holder, which both essentially have the shape of an "eight" and whose longitudinal directions extend transversely to the longitudinal axis of the brush member. In this bristle field the free ends of the bristles are bounded by two enveloping surfaces which are inclined continuously with respect to the holder surface of the bristle holder but which do not intersect one another at the location of a holder axis and whose line of intersection does not extend transversely to the longitudinal axis of the brush member but exactly parallel to the longitudinal axis of the brush member. The form of the bristle field of the variant of the known toothbrush inter alia has the advantage, described in the document U.S. Pat. No. 4,399,582 A, that both the upper row of teeth and the lower row of teeth of a user can be cleaned at the same time and that partly a comparatively good access to hard-to-get-at areas can be obtained. However, particularly on account of the orientation of the line of intersection of the two enveloping surfaces parallel to the longitudinal axis of the brush member the variant known from U.S. Pat. No. 4,399,582 A is in no way suitable for a correct positioning of the bristle field with respect to a tooth to be cleaned, in contradistinction to a toothbrush in accordance with the invention which is very suitable for this owing to the characteristic features of the invention.

Moreover, it is to be noted that a toothbrush in several variants is known from the document DE 44 38 731 A1. In this known toothbrush the brush member end which is remote from the grip member does not carry one bristle holder but it carries two bristle holders which are each adjustable with respect to the holder axis which extends transversely to the longitudinal axis of the brush member. In a variant of this known toothbrush, shown in FIG. 9b of the document DE 44 38 731 A1, a part the bristles of each of the two bristle fields arranged around the holder axis has free ends bounded by two non-stepped enveloping surfaces which are steadily inclined with respect to the holder surface of each bristle holder but which do not intersect one another at the location of the holder axis but along a line of intersection in an area laterally offset from the holder axis. Furthermore, in this variant of the known toothbrush the line of intersection of the two enveloping surfaces does not extend transversely to the longitudinal axis of the brush member but parallel to the longitudinal of the brush member. In this variant of the known toothbrush, which merely because of the fact that the brush member has two bristle holders is of a totally different construction than the toothbrush in accordance with the invention, it is to be noted also that the fact that the free ends of the bristles of both bristle fields are bounded by two enveloping surfaces which are inclined relative to one another, has no positive effect on an accurate positioning of a brush head with respect to the curved tooth surfaces, which is definitely the case for a toothbrush in accordance with the invention owing to the characteristic features of the invention.

In a toothbrush in accordance with the invention it has proved to be very advantageous if the free ends of all the bristles of the bristle field are bounded by two non-stepped enveloping surfaces which are inclined continuously with respect to the holder surface of the bristle holder. In this way it is achieved that substantially the entire bristle field assists in its positioning with respect to the curved surface of a tooth, which is very advantageous for a proper cleaning performance of the bristles of the bristle field.

In a toothbrush in accordance with the invention it has proved to be particularly advantageous if the two enveloping surfaces are formed by two enveloping planes. This is advantageous in view of a particularly simple implementation of the level variation of the bristle ends, i.e. of the bristle field topography.

When the bristle holder is in its center position in a toothbrush in accordance with the invention, the line of intersection of the two enveloping surfaces may extend at an angle , in a range between 60° and 120°, relative to the longitudinal axis of the brush member. However, it has proved to be very advantageous if, when the bristle holder is in its center position, the line of intersection of the two enveloping surfaces and the longitudinal axis of the brush member include an angle which lies in a range between 80° and 100°. Such an embodiment has proved to be very advantageous in order to achieve an optimum positioning action.

In order to achieve a satisfactory positioning action it has proved to be very advantageous if the angle has a value of 90°. This provides a particularly good positioning action, as a result of which particularly good cleaning results are obtained.

In a toothbrush in accordance with the invention it can also be advantageous if a tangential plane to each of the two enveloping surfaces can be construed at the location of their line of intersection, and the two tangential planes include an angle $\beta$ with one another, which angle lies in a range between 110° and 175°. However, it has proved to be very advantageous if a tangential plane to each of the two enveloping surfaces can be construed at the location of their line of intersection, and the two tangential planes include an angle $\beta$ with one another, which angle lies in a range between 150° and 170°. This construction is also advantageous in order to optimize the positioning action and, at the same time, to optimize the cleaning results.

In the above context it has proved to be particularly advantageous if the angle $\beta$ has a value of 160°. Such an embodiment has proved to be a particularly favorable solution in practical tests.

In a toothbrush in accordance with the invention, in which the brush member in addition comprises an interdental bristle holder, which is movable beyond a center position and is disposed adjacent the bristle holder substantially in the longitudinal direction of the brush member, which interdental bristle holder is mounted on the brush member so as to be movable and has a further holder surface, and from which at the location of the further holder surface interdental bristles project transversely to the further holder surface, which interdental bristles together form an interdental bristle field and are disposed at opposite sides of a central plane which extends transversely to the longitudinal axis of the brush member—as is known from the afore-cited DE 43 09 035 A1—it has further proved to be very advantageous the free ends of the interdental bristles are bounded by two non-stepped enveloping surfaces which are inclined continuously with respect to the further holder surface of the interdental bristle holder, which enveloping surfaces extend as a roof-shape with respect to the further holder surface of the interdental bristle holder and intersect one another along a further line of intersection at the location of the central plane, and the further line of intersection of the two further enveloping surfaces extends transversely to the longitudinal axis of the brush member. In such an embodiment of a toothbrush in accordance with the invention the interdental bristles assist at least partly in positioning with respect to the teeth to be cleaned, the provision of interdental bristles shaped in accordance with the invention having an additional positive effect on the cleaning action in the interdental spaces.

In a toothbrush as defined in the preceding paragraph it has proved to be very advantageous if the two further enveloping surfaces are formed by two further enveloping planes. This is advantageous in view of a particularly simple implementation of the level variation of the interdental-bristle ends, i.e. of the interdental-bristle field topography.

In a toothbrush having an interdental bristle field, when the interdental bristle holder is in its center position, the further line of intersection of the two further enveloping surfaces and the longitudinal axis of the brush member may include an angle $\gamma$ which lies in a range between 60° and 120°. However, it has proved to be very advantageous if, when the interdental bristle holder is in its center position, the further line of intersection of the two further enveloping surfaces and the longitudinal axis of the brush member include an angle $\gamma$ which lies in a range between 80° and 100°. Such an embodiment has proved to be very advantageous for an optimum contribution of the interdental bristles to the positioning action.

For such an optimum contribution of the interdental bristles to the positioning action it has proved to be particularly advantageous if the angle $\gamma$ has a value of 90°. In this way, the positioning action is assisted in a particularly suitable manner.

In a toothbrush having an interdental bristle field it can also be advantageous if a further tangential plane to each of the two further enveloping surfaces can be construed at the location of the further line of intersection, and the two further tangential planes include an angle $\delta$ with one another, which angle lies in a range between 60° and 175°. However, it has proved to be very advantageous if a further tangential plane to each of the two further enveloping surfaces can be construed at the location of the further line of intersection, and the two further tangential planes include an angle $\delta$ with one another, which angle lies in a range between 110° and 130°. This is very advantageous for a satisfactory cleaning of the interdental spaces.

In the above context it has proved to be particularly advantageous if the angle δ has a value of 120°. Such an embodiment has proved to be particularly favorable in practical tests.

According to the invention, in order to achieve the object mentioned in the introduction with a brush member of the type defined in the second paragraph, the free ends of at least a part of the bristles of the bristle field arranged around the holder axis are bounded by two non-stepped enveloping surfaces which are inclined continuously with respect to the holder surface of the bristle holder, which enveloping surfaces are arranged substantially in a V-shape and intersect one another along a line of intersection at the location of the holder axis, and the line of intersection of the two enveloping surfaces extends transversely to the longitudinal axis of the brush member. Thus, it is achieved that the variation in level of the free ends of the bristles of the bristle field of a toothbrush in accordance with the invention can be without steps and the free ends of the bristles can be formed so as to be situated at a continuously varying level, and the continuous variation in level of the free ends of the bristles of the bristle field is essentially mirror-symmetrical with respect to the holder axis and the line of intersection of the two enveloping surfaces, which extends transversely to the longitudinal axis of the brush member. This has proved to be favorable for a proper positioning of the bristle field with respect to the curved tooth surfaces, which surfaces are essentially mirror-symmetrical relative to a surface tangent which is also oriented transversely to the longitudinal axis of the brush member, and consequently for a satisfactory cleaning action of the bristles of the bristle field. Furthermore, it is to be noted that a construction in accordance with the invention has also proved to be advantageous in view of a simple implementation of the level variation of the bristle ends, i.e. of the bristle field topography.

With respect to a brush member in accordance with the invention reference is also made to the two afore-mentioned documents U.S. Pat. No. 4,399,582 A and DE 44 38 731 A1, because the argumentation given hereinbefore with respect to a toothbrush in accordance with the invention likewise apply to a brush member in accordance with the invention.

In a brush member in accordance with the invention it has proved to be very advantageous if the free ends of all the bristles of the bristle field are bounded by two non-stepped enveloping surfaces which are inclined continuously with respect to the holder surface of the bristle holder. In this way it is achieved that substantially the entire bristle field assists in its positioning with respect to the curved surface of a tooth, which is very advantageous for a proper cleaning performance of the bristles of the bristle field.

In a brush member in accordance with the invention it has proved to be particularly advantageous if the two enveloping surfaces are formed by two enveloping planes. This is advantageous in view of a particularly simple implementation of the level variation of the bristle ends, i.e. of the bristle field topography.

When the bristle holder is in its center position in a brush member in accordance with the invention, the line of intersection of the two enveloping surfaces may extend at an angle , in a range between 60° and 120°, relative to the longitudinal axis of the brush member. However, it has proved to be very advantageous if, when the bristle holder is in its center position, the line of intersection of the two enveloping surfaces and the longitudinal axis of the brush member include an angle which lies in a range between 80° and 100°. Such an embodiment has proved to be very advantageous in order to achieve an optimum positioning action.

In order to achieve a satisfactory positioning action it has proved to be very advantageous if the angle has a value of 90°. This provides a particularly good positioning action, as a result of which particularly good cleaning results are obtained.

In a brush member in accordance with the invention it can also be advantageous if a tangential plane to each of the two enveloping surfaces can be construed at the location of their line of intersection, and the two tangential planes include an angle β with one another, which angle lies in a range between 110° and 175°. However, it has proved to be very advantageous if a tangential plane to each of the two enveloping surfaces can be construed at the location of their line of intersection, and the two tangential planes include an angle β with one another, which angle lies in a range between 150° and 170°. This measure in accordance with the invention is also advantageous in order to optimize the positioning action and, at the same time, to optimize the cleaning results.

In the above context it has proved to be particularly advantageous if the angle β has a value of 160°. Such an embodiment has proved to be a particularly favorable solution in practical tests.

In a brush member in accordance with the invention, in which the brush member in addition comprises an interdental bristle holder, which is movable beyond a center position and is disposed adjacent the bristle holder substantially in the longitudinal direction of the brush member, which interdental bristle holder is mounted on the brush member so as to be movable and has a further holder surface, and from which at the location of the further holder surface interdental bristles project transversely to the further holder surface, which interdental bristles together form an interdental bristle field and are disposed at opposite sides of a central plane which extends transversely to the longitudinal axis of the brush member—as is known from the afore-cited DE 43 09 035 A1—it has further proved to be very advantageous the free ends of the interdental bristles are bounded by two non-stepped enveloping surfaces which are inclined continuously with respect to the further holder surface of the interdental bristle holder, which enveloping surfaces extend as a roof-shape with respect to the further holder surface of the interdental bristle holder and intersect one another along a further line of intersection at the location of the central plane, and the further line of intersection of the two further enveloping surfaces extends transversely to the longitudinal axis of the brush member. In such an embodiment of a brush member in accordance with the invention the interdental bristles assist at least partly in positioning with respect to the teeth to be cleaned, the provision of interdental bristles shaped in accordance with the invention having an additional positive effect on the cleaning action in the interdental spaces.

In a brush member as defined in the preceding paragraph it has proved to be very advantageous if the two further enveloping surfaces are formed by two further enveloping planes. This is advantageous in view of a particularly simple implementation of the level variation of the interdental-bristle ends, i.e. of the interdental-bristle field topography.

In a brush member having an interdental bristle field, when the interdental bristle holder is in its center position, the further line of intersection of the two further enveloping surfaces and the longitudinal axis of the brush member may include an angle γ which lies in a range between 60° and 120°. However, it has proved to be very advantageous if, when the interdental bristle holder is in its center position, the further line of intersection of the two further enveloping surfaces and the longitudinal axis of the brush member include an angle γ which lies in a range between 80° and 100°. Such an embodiment has proved to be very advantageous for an optimum contribution of the interdental bristles to the positioning action.

For such an optimum contribution of the interdental bristles to the positioning action it has proved to be particularly advantageous if the angle γ has a value of 90°. In this way, the positioning action is assisted in a particularly suitable manner.

In a brush member having an interdental bristle field it can also be advantageous if a further tangential plane to each of the two further enveloping surfaces can be construed at the location of the further line of intersection, and the two further tangential planes include an angle δ with one another, which angle lies in a range between 60° and 175°. However, it has proved to be very advantageous if a further tangential plane to each of the two further enveloping surfaces can be construed at the location of the further line of intersection, and the two further tangential planes include an angle δ with one another, which angle lies in a range between 110° and 130°. This is very advantageous for a satisfactory cleaning of the interdental spaces.

In the above context it has proved to be particularly advantageous if the angle δ has a value of 120°. Such an embodiment has proved to be particularly favorable in practical tests.

The above-mentioned as well as further aspects of the invention will become apparent from the embodiments described hereinafter by way of examples and will be elucidated by means of these embodiments.

The invention will now be described in more detail with reference to the drawings, which show some embodiments, given by way of examples to which the invention is not limited.

DESCRIPTION OF THE PREFERRED EMBODIMENTS

Figure 1:
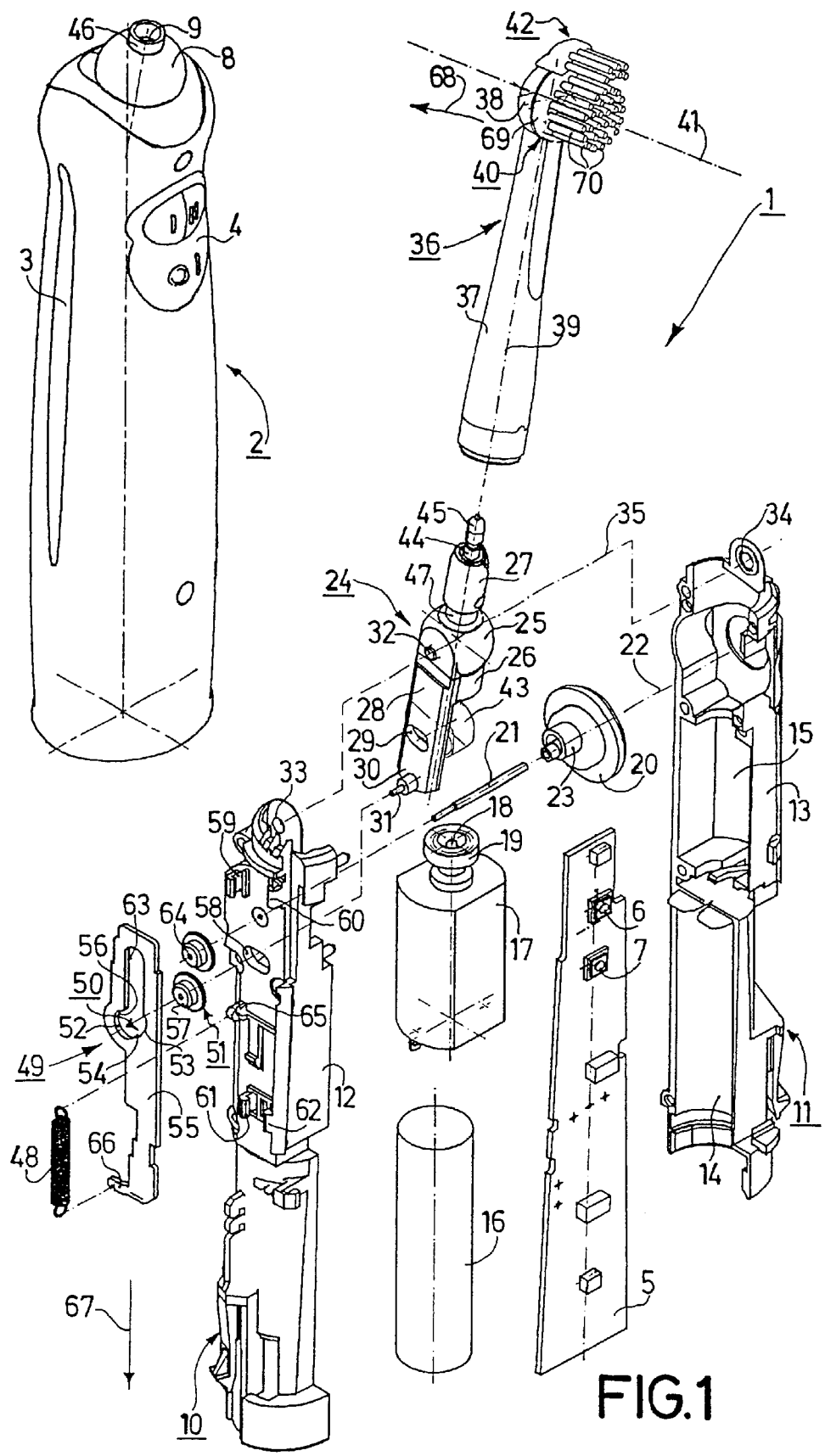
FIG. 1 is an exploded view of the relevant parts of a toothbrush in accordance with a first embodiment of the invention, which toothbrush comprises a brush member in accordance with a first embodiment of the invention.

FIG. 1 shows the relevant parts of a toothbrush 1 in accordance with the invention. The toothbrush 1 has a comparatively rigid plastic housing 2, which forms a grip member of the toothbrush 1. Connected to the housing 2 are two strip-shaped side grips, of which only one side grip 3 is visible in FIG. 1, an elastic plastic switch cover 5, which is integral with the housing 2 and underneath which two switches 6 and 7 on a printed circuit board 5 accommodated in the housing 2 are arranged, and an elastic plastic dome-shaped cover 8, which is also integral with the housing 2 and which has an opening 9, whose purpose will be described hereinafter, at its free end.

The housing 2 accommodates a first stationary support 10 and a second stationary support 11, both made of a rigid plastic. The two carrier parts 10 and 11 are connected in a manner not shown. The two carrier parts 10 and 11 each have a lateral surface 12 and 13, respectively. The printed circuit board 5 is mounted on the two lateral surfaces 12 and 13. The two carrier parts 10 and 11 each have two holder chambers, of which only a first holder chamber 14 and a second holder chamber 15 of the second carrier part 11 are visible in FIG. 1. In conjunction with the corresponding first holder chamber of the first carrier part 10 the first holder chamber 14 of the second carrier part 11 forms a holder space for a rechargeable battery 16, which can be charged via a charging circuit provided on the printed circuit board 5. In conjunction with the corresponding second holder chamber of the first carrier part 10 the second holder chamber 14 of the second carrier part 11 forms a holder space to accommodate an electric drive motor 17. In a manner not shown, the drive motor 17 is electrically connected to the printed circuit board 5 and can be energized by a power supply circuit on the printed circuit board 5, which circuit is powered by the battery 16.

The drive motor 17 has a drive shaft 18, which in the present case carries a pinion 19, which is locked in rotation to this shaft. A toothed wheel 20, shown only diagrammatically in FIG. 1, can be driven by the pinion 19. The toothed wheel 20 is mounted so as to be rotatable about an axis 22 by means of a spindle 21 mounted in the two stationary carrier parts 10 and 11. A hollow cylindrical eccentric part 23, which is disposed eccentrically relative to the axis 22, is integral with the toothed wheel 20.

The toothbrush 1 comprises a brush holder 24 which is movable relative to the first stationary carrier part 10 and also relative to the second stationary part 11. The brush holder 24 comprises a largely spherical portion 25 whose side facing the drive motor 17 is integrally connected to a substantially cylindrical portion 26 and whose side remote from the drive motor 17 is integrally connected to a substantially cylindrical coupling portion 27. The brush holder 24 further comprises an arm 28 connected to the spherical portion 25 and to the cylindrical portion 26. The arm 28 has a slot 29 to allow the passage of the spindle 21. The free end 30 of the arm 28 carries a trunnion 31, which is integral with the arm 28 and which projects laterally from the arm 28, the purpose of this trunnion being described hereinafter.

In the toothbrush 1 as shown in FIG. 1 the movable brush holder 24 is mounted so as to be pivotable relative to the two stationary carrier parts 10 and 11. For this purpose, the brush holder 24 comprises two trunnions, of which only one trunnion 32 is visible in FIG. 1. The visible first trunnion 32 engages a first bore 33 in the first carrier part 10. The non-visible trunnion engages a second bore 34 in the second carrier part 11. In this way, the brush holder 24 is mounted so as to be pivotable about an axis 35 relative to the two stationary carrier parts 10 and 11. The brush holder 24 is pivotable between a normal position and a deflection position.

The brush holder 24 is adapted to hold a brush member 36. The brush 20 member 36 is or can be connected to the housing 2 of the toothbrush 1, which housing forms a grip member, with the aid of the brush holder 24. The brush member 36 comprises a tubular portion 37 and a disc portion 38 which is integrally connected to the tubular portion 37 at that end of the tubular portion 37 which is remote from the housing 2. The tubular portion 37 and, consequently, the brush member 36 have a longitudinal axis 39. A bristle holder is mounted on the disc portion 38 so as to be movable with respect to a holder axis 41 which extends transversely to the longitudinal axis 39, in the present case exactly perpendicularly to the longitudinal axis 39, i.e. the bristle holder 40 is pivotable about the holder axis 41, which extends perpendicularly to the longitudinal axis 39 of the brush member 36, between two deflection positions through a center position.

Moreover, an interdental bristle holder 42 is mounted on the disc portion 38 so as to be movable, i.e. so as to be reciprocatingly movable transversely to the longitudinal axis 39 of the brush member 36, and is coupled in driving engagement with the bristle holder 40 which is drivable for reciprocation along a circularly arcuate path, as a result of which the interdental bristle holder 41 is driven to reciprocate transversely to the longitudinal axis 39 of the brush member 36 when the bristle holder 40 is reciprocated along the circularly arcuate path.

The bristle holder 40 is driven by the drive motor 17 via the afore-mentioned pinion 19, the toothed wheel 20 and the eccentric part 23. The eccentric part 23 engages in a slot formed in a block-shaped projection 43 of a connecting rod 44 and extending transversely to the longitudinal axis 39 of the brush member 36. The connecting rod 44 is integral with the projection 43. The connecting rod 44 extends through a bore in the brush holder 24, which bore passes through the cylindrical portion 26, the spherical portion 25 and the cylindrical coupling portion 27.

When the brush member 36 is mounted on the brush holder 24 the tubular portion 37 is suitably mechanically coupled to the cylindrical coupling portion 27 via a bayonet coupling, not shown. Furthermore, the cross-sectionally triangular free end 45 of the connecting rod 44 engages in a coupling recess in a driving rod, not shown, which is mounted in the tubular portion 37 so as to be movable substantially along the longitudinal axis 39. The end of the drive rod, not shown, which is remote from the connecting rod 44 is in driving engagement with the bristle holder 40 via a pivotal joint which is disposed eccentrically relative to the holder axis 41.

With respect to the construction of the brush member 36 reference can be made to published European Patent bearing the number WO 97/24079 which corresponds to and claims the priority of the Applicants Austrian patent Application bearing the Application number A 2112/95, herewith incorporated by reference.

In the assembled condition of the toothbrush 1 the brush holder 24 extends with its cylindrical coupling portion 27 through the opening 9 in the cover 8 made of an elastic plastic, a hollow cylindrical portion 46 of the cover 8 being in sealing engagement with a cylindrical groove 47 of the coupling portion 27 of the brush holder 24 so as to preclude ingress of moisture or water into the housing interior.

As already stated hereinbefore, the brush holder 24 of the toothbrush 1, including the brush member 36 it holds, is pivotable between a normal position and a deflection position. In the toothbrush 1 a spring 48 has been provided, which spring is formed by a helical tension spring acting between the first stationary carrier part 10 and the brush holder 24. The brush holder 24 can be held in its normal position by means of the spring force of the spring 48. When a given limit value of the cleaning force exerted on the brush member 36 during operation is exceeded the brush holder 24, including the brush member 36 held by it, is movable into its deflection position against the spring force of the spring 48.

In addition to the spring 48 acting between the stationary carrier part 10 and the brush holder 24 the toothbrush 1 comprises a link-motion device 49, which acts between said parts and is loaded by the spring 48, in order to obtain a desired force characteristic. The link-motion device 49 comprises a sliding surface 50 and a follower 51, which are movable relative to one another. The sliding surface 50 of the link-motion 49 comprises two sliding-surface portions 52 and 53, i.e. a first sliding-surface portion 52 and a second sliding-surface portion 53. The two sliding-surface portions 52 and 53 adjoin one another by an edge-like transition portion 54.

The link-motion device 49 further comprises a slider 55 having a cut-out 56. The two sliding-surface portions 52 and 53 of the sliding surface 50 of the link-motion device 49 are formed by two bounding surface portions of the cut-out 56. The follower 51 of the link-motion device 49 engages in the cut-out 56. The follower 51 comprises a rotatably mounted link-motion roller 57, which is rotatably mounted on the trunnion 31 of the brush holder 24, for which purpose the trunnion 31 is passed through a slot 58 formed for this purpose in the first carrier part 10. Thus, by means of the trunnion 31 the follower 51 is stationarily mounted on the brush holder 24 and is rotatable relative to the brush holder 24.

The slider 55 is retained on the first stationary carrier part 10 by means of four hooks 59, 60, 61 and 62 which project from the first carrier part 10. Thus, the slider is slidably guided on the first carrier part 10. for slidably guiding the slider 55 In the present case the slider 55 has a single slot 63 for slidably guiding the slider 55, which slot in the present case changes into the cut-out 56. The slot 63 is engaged by a guide roller 64, which is rotatably mounted on the spindle 21, which for this purpose extends through the first carrier part 10. In this way, the guide roller 64 is stationarily but rotatably mounted on the first carrier part 10. By means of the slot 63 and the guide roller 64 the slider 55 is guided with a comparatively low friction at the location of the sliding surface 50 and the link-motion roller 57. The slider 55 is guided so as to be slidable in its longitudinal direction by means of the two hooks 61 and 62 in the slider area which is remote from the slot 63.

In the toothbrush 1 the spring 48 is arranged between the first stationary carrier part 10 and the slider 55. For this purpose the first stationary carrier part 10 comprises a coupling projection 65 and the slider 55 has a laterally projecting further coupling projection 66. The spring 58 is attached to both coupling projections 65 and 66.

During normal operation of the toothbrush 1 the brush holder 24, together with the brush member 36 it holds, is in the normal position shown in FIG. 1, in that the spring 48 coupled to the first stationary carrier part 10 exerts an adequate force on the slider 55 of the link-motion device 49, as a result of which an adequate force is exerted on the link-motion roller 57 via first sliding-surface portion 52 which in this case cooperates with the link-motion roller 57 and, consequently, the link-motion roller 57 remains applied to the sliding-surface portion 52 and, as a result, the brush holder 24, together with the brush member 36 it carries, is held in its normal position. However, if during operation of the toothbrush 1 an excessive cleaning force, which exceeds the afore-mentioned limit value, is exerted on the brush member 36, the link-motion roller 57 will exert such a large force on the first sliding-surface portion 52 that the link-motion roller 57 is moved past the edge-like transition portion 54 between the two sliding-surface portions 52 and 53, the slider 55 of the link-motion device 49 being moved in the direction indicated by the arrow 67 in FIG. 1 opposed by the force of the spring 48 and, at the same time, the brush holder 24 and the brush member 36 carried by this holder being moved into its deflection position in the direction indicated by the arrow 68 which is also shown in FIG. 1, as a result of which the user is given a signal that he applies an excessive cleaning force. When this excessive cleaning force is reduced the slider 55 of the link-motion device 49 is moved in a direction opposite to that indicated by the arrow 67 in FIG. 1 by the force of the spring 48, as a result of which the link-motion roller 57 again enters into operative engagement with the first sliding surface portion 52, causing the brush holder 24 and hence the brush member 36 it carries to be moved back into its normal position in a direction opposite to that indicated by the arrow 68 in FIG. 1.

Figure 2:
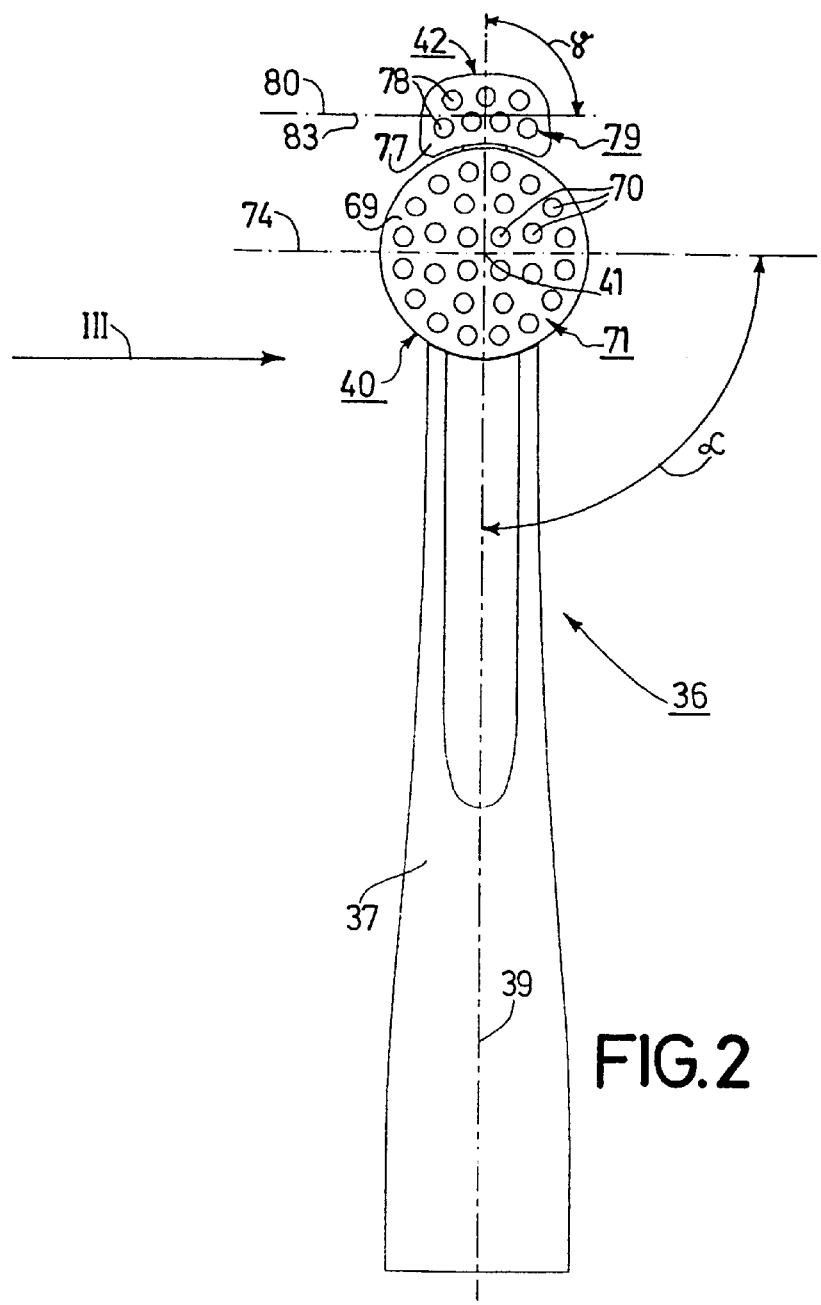
FIG. 2 is a plan view to twice the full-size scale showing the brush member in accordance with the first embodiment of the invention of the toothbrush shown in FIG. 1.
Figure 3:
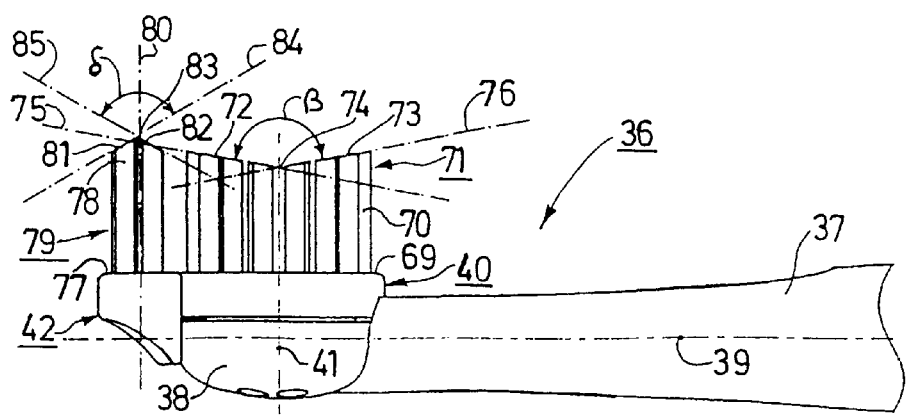
FIG. 3 shows the brush member in accordance with the first embodiment of the invention in a side view to the same scale as FIG. 2 and taken at the arrow III in FIG. 2.

As already stated hereinbefore, the brush member 36 of the toothbrush 1 as shown in FIG. 1 comprises a bristle holder 40 and an interdental bristle holder 42, the bristle holder 40 being pivotable about the holder axis 41 between two deflection positions via the center position and the interdental bristle holder 42 being reciprocatingly movable relative to the longitudinal axis 39 between two deflection positions via a center position and thus being each time also movable beyond the center position. FIGS. 1, 2 and 3 show the bristle holder 40 and the interdental bristle holder 42 in their center positions.

The bristle holder 40 has a holder surface 69 which extends transversely to the holder axis 41. In the area of the holder surface 69 bristles 70 project from the bristle holder 40 transversely to the holder surface 69. In the present case the bristles 70 extend perpendicularly to the holder surface 69 of the bristle holder 40. The bristles 70 together form a bristle field 71 and are arranged around the holder axis 41. The peripheral bristles of the bristles 70 situated at the periphery of the bristle field 71 are longer than the bristles situated in the inner part of the bristle field 71. As is apparent from FIG. 2, the bristles 70 of the bristle field 71 are arranged in tufts, which are each represented as a circle in FIG. 2. In the brush member 36 as shown in FIG. 2, the tufts are arranged along three mutually concentric circles, a total of sixteen tufts being disposed on the outer circle, a total of eight tufts on the central circle and a total of four tufts on the inner circle. It is to be noted that in a full-size brush member 36 the bristle holder 40 has a diameter of approximately 11.8 mm, the outer circle of tufts has a diameter of approximately 11.2 mm, the central circle of tufts has a diameter of 7.2 mm, and the inner circle of tufts has a diameter of 3.2 mm, the tufts having a diameter of 1.3 mm. It is to be noted also that the longest bristles 70 of the bristle field 71 have a free length of approximately 8.0 mm with respect to the holder surface 69 and the shortest bristles 70 of the bristle field 71 have a free length of approximately 6.9 mm with respect to the holder surface 69.

As is apparent from FIG. 3, the toothbrush 1 shown in FIG. 1, i.e. the brush member 36 of this toothbrush 1, has the advantage that the free ends of all the bristles 70 of the bristle field 71, which surround the holder axis 41 are bounded by two non-stepped enveloping surfaces 72 and 73, which are inclined continuously with respect to the holder surface 69 of the bristle holder 40 and which extend in a V-shape with respect to the holder surface 69 of the bristle holder 40 and which intersect one another along a line of intersection 74 at the location of the holder axis 41. The line of intersection 74 of the two enveloping surfaces 72 and 73 extends suitably transversely to the longitudinal axis 39 of the brush member 36. In the toothbrush 1 as shown in FIG. 2 and the brush member 36 as shown in FIGS. 2 and 3, the two enveloping surfaces 72 and 73 are suitably formed by two enveloping planes. When the bristle holder 40 is in its center position, as is shown in FIGS. 1, 2 and 3, the line of intersection 74 of the two enveloping surfaces 72 and 73, which are each formed by a enveloping plane, is disposed at an angle with respect ton the longitudinal axis 39 of the brush member 36, which angle is suitably 90° in the present case.

A tangential plane 75 or 76, each represented as a dash-dot line in Figure, to each of the two enveloping surfaces can be construed at the location of the line of intersection 74. The two tangential planes 75 and 76 include an angle $\beta$ with one another, which in the present case suitably has a value of 160°.

With respect to the variation in level of the free ends of the bristles 70 of the bristle field 71 it is to be noted that the level variation of the free ends of the bristles 70 of the bristle field 71 is implemented in a milling operation, in a manner which has been known per se since long.

The interdental bristle holder 42 has a further holder surface 77, which in the present case extends parallel to the holder surface 69 of the bristle holder 40, but this need not necessarily so because the further holder surface of the interdental bristle holder 42 can alternatively be inclined relative to the holder surface 69 of the bristle holder 40. In the area of the further holder surface 77 interdental bristles 78 project from the interdental bristle holder 42 transversely to the further holder surface 77. In the present case the interdental bristles 78 extend perpendicularly to the further holder surface 77 of the interdental bristle holder 42. The interdental bristles 78 together form an interdental bristle field 79. The interdental bristles 78 are disposed at opposite sides of a central plane 80 which extends transversely, in the present case exactly perpendicularly, to the longitudinal axis 39 of the brush member 36.

In the toothbrush 1 as shown in FIG. 1 and its brush member 36 as shown in FIGS. 2 and 3 the free ends of the interdental bristles 78 are suitably bounded by two further non-stepped enveloping surfaces 81 and 82 which are inclined relative to the further holder surface 77 of the interdental bristle holder 42. The two further enveloping surfaces 81 and 82 extend as a roof-shape with respect to the further holder surface 77 of the interdental bristle holder 42. The two further enveloping surfaces 81 and 82 intersect one another in a further line of intersection 83 at the location of the central plane 80. The further line of intersection 83 of the two further enveloping surfaces 81 and 82 now extends transversely, in the present case exactly perpendicularly, to the longitudinal axis 39 of the brush member 36. As is apparent from FIG. 3, the two further enveloping surfaces 81 and 82 are formed by two further enveloping planes in the present case.

When the interdental bristle holder 42 is in its center position the further line of intersection 83 of the two further enveloping surfaces 81 and 82, as is shown in FIG. 2, extends at an angle γ with respect to the longitudinal axis 39 of the brush member 36, which angle has a value of 90° in the present case.

As is apparent from FIG. 3, a further tangential plane 84 or 85, respectively, each represented as a dash-dot line in FIG. 3, to each of the two further enveloping surfaces 81 and 82, each formed by an enveloping plane, can be construed at the location of the further line of intersection 83. The two further tangential planes 84 and 85 enclose an angle δ with one another, which in the present case has a value of 120°.

With respect to the variation in level of the free ends of the interdental bristles 78 of the interdental bristle field 79 it is to be noted that the level variation of the free ends of the interdental bristles 78 of the interdental bristle field 79 is also implemented in a milling operation.

In the toothbrush 1 as shown in FIG. 1 and its turn-on 36 as shown in FIGS. 2 and 3 it has advantageously been achieved that the variation in level of the free ends of the bristles 70 of the bristle field 71 is without an step and that the free ends of the bristles 70 are formed so as to extend at a continuously varying level, the continuously varying level of the free ends of the bristles 70 of the bristle field 71 being essentially mirror symmetrical with respect to the holder axis 41 and the line of intersection 74 of the two enveloping surfaces 72 and 73, which line extends transversely to the longitudinal axis 39 of the brush member 36. This structure has proved to be favorable for a correct positioning of the bristle field 71 with respect to the curved tooth surfaces and consequently for a satisfactory cleaning action of the bristles 70 of the bristle field 71. Furthermore, with the structure described in the foregoing it is achieved that the interdental bristles 78 positively assists in the positioning of the bristles 70 of the bristle field 71 with respect to the teeth to be cleaned, which is advantageous for a proper cleaning action of the bristles 70 of the bristle field 71, the provision of interdental bristles 78 shaped as described in the foregoing also resulting in a very good cleaning action in the interdental spaces by means of the interdental bristles 78.

Figure 4:
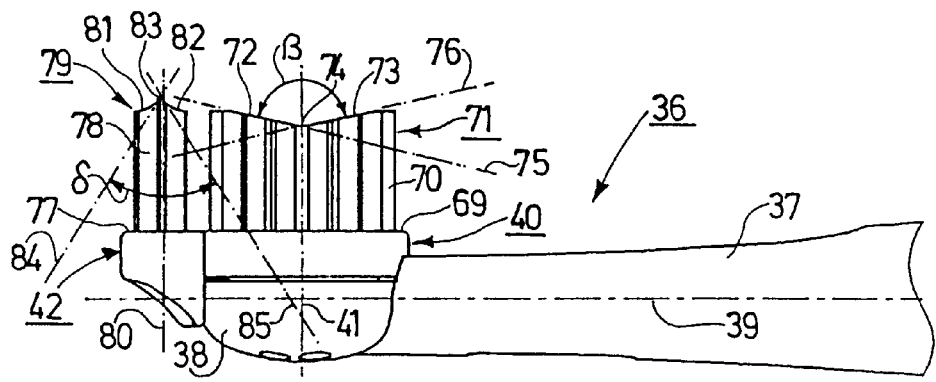
FIG. 4 shows a brush member in accordance with a second embodiment of the invention in a similar way as in FIG. 3.

FIG. 4 shows a brush member 36 in accordance with a second embodiment of the invention. The brush member 36 as shown in FIG. 4 has two differences with respect to the brush member 36 as shown in FIGS. 2 and 3. In the brush member 36 as shown in FIG. 4 the two enveloping surfaces 72 and 73 do not extend into the outer peripheral area of the bristle field 71, so that at a least a part of the bristles 70 situated in the outer peripheral area of the bristle field 71 is not bounded by the two enveloping surfaces 72 and 73 but by two enveloping surfaces which extend parallel to the holder surface 69. Moreover, in the brush member 36 a shown in FIG. 4 the free ends of the interdental bristles 78 are not bounded by two further enveloping surfaces but by two concave further enveloping surfaces 81 and 82.

Figure 5:
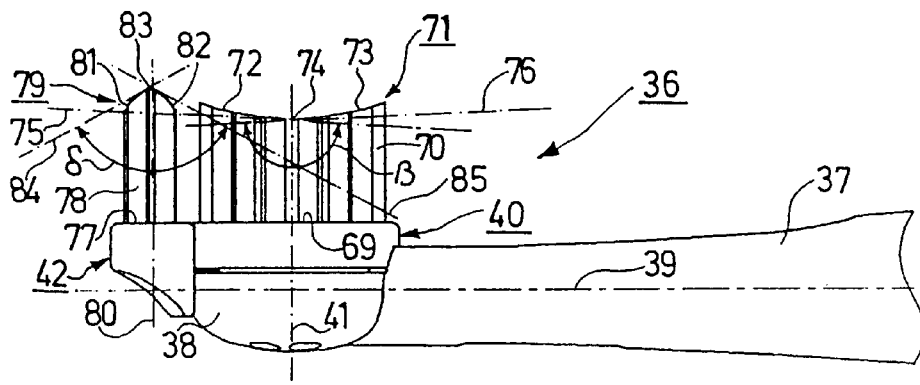
FIG. 5 shows a brush member in accordance with a third embodiment of the invention in a similar way as in FIGS. 3 and 4.

In the brush member 36 shown in FIG. 5, in accordance with a third embodiment of the invention, the free ends of the bristles 70 of the bristle field 71 are bounded by two curved, i.e. concave, enveloping surfaces 72 and 73. The free ends of the interdental bristles 78 of the interdental bristle field 79 are also bounded by two curved, in the present case convex, further enveloping surfaces 81 and 82.

Figure 6:
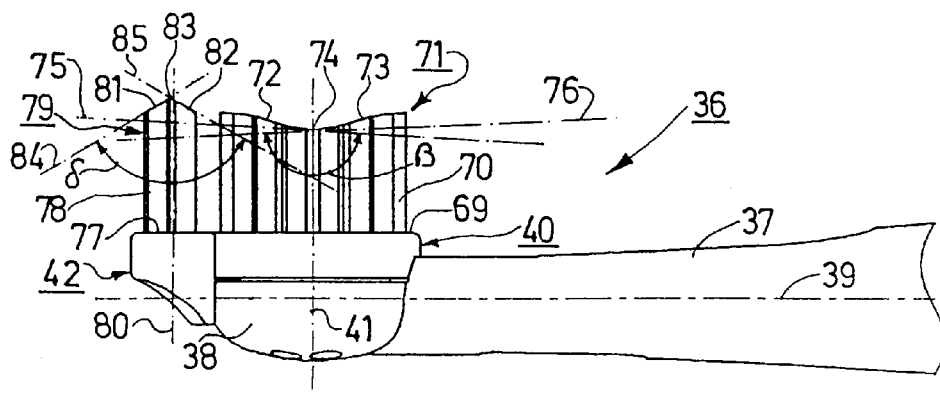
FIG. 6 shows a brush member in accordance with a fourth embodiment of the invention in a similar way as in FIGS. 3, 4 and 5.

In the brush member 36 shown in FIG. 6, in accordance with a fourth embodiment of the invention, the free ends of the bristles 70 of the bristle field 71 are bounded by two curved enveloping surfaces 72 and 73, which enveloping surfaces 72 and 73 are convex at the location of the longer bristles 70 and concave at the location of the shorter bristles 70. The free ends of the interdental bristles 78 in the brush member 36 as shown in FIG. 6 are bounded in the same way as in the brush member 36 as shown in FIGS. 2 and 3.

Figure 7:
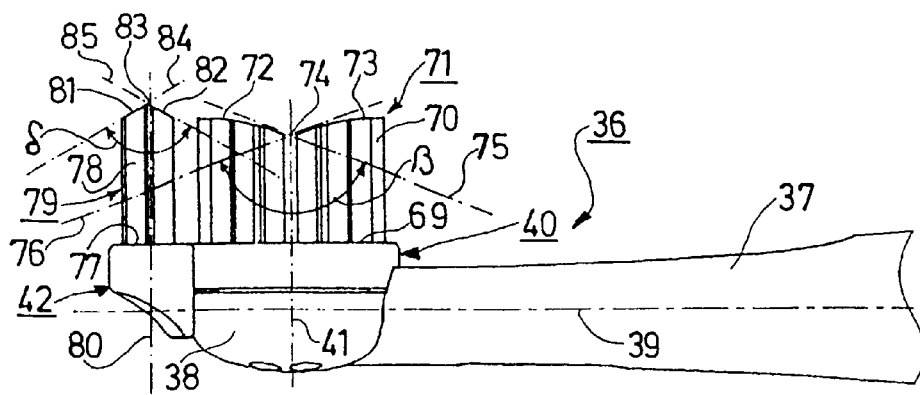
FIG. 7 shows a brush member in accordance with a fifth embodiment of the invention in a similar way as in FIGS. 3, 4, 5 and 6.

In the brush member 36 shown in FIG. 7, in accordance with a fifth embodiment of the invention, the free ends of the bristles 70 of the bristle field 71 are bounded by two curved, i.e. convex, enveloping surfaces 72 and 73. The free ends of the interdental bristles 78 of the interdental bristle field 79 are bounded in the same way as in the brush member 36 as shown in FIGS. 2 and 3.

The invention is not limited to the embodiments described hereinbefore. For example, the free ends of the bristles of a bristle field on a bristle holder may be bounded by two enveloping surfaces which are arranged substantially in a V-shape and which are each slightly undulate. Moreover, a bristle field on a bristle holder need not be circularly cylindrical as in the embodiments described hereinbefore, but a bristle field can also be oval, substantially rectangular or quadriform in a cross-section parallel to the holder surface. Furthermore, the bristle holder can be moved through its center position with a rotary movement in a steady direction of rotation instead of with a reciprocatory oscillating movement.

What is claimed is:

1. A toothbrush comprising a grip member and a brush member connected to the grip member, which brush member has a longitudinal axis and comprises a brush holder pivotably mounted to be pivotable between a normal position and a deflection position about an axis, and whose end remote from the grip member carries a bristle holder, which bristle holder is mounted on the brush member so as to be pivotable between a normal position and a deflection position about a holder axis which extends transversely to the longitudinal axis, and which bristle holder has a holder surface which extends substantially transversely to the holder axis and from which in the area of the holder surface, bristles project transversely to the holder surface, which bristles together form a bristle field and are arranged around the holder axis, wherein:

the free ends of most of the bristles of the bristle field arranged around the holder axis are bounded by only two non-stepped enveloping surfaces which are inclined continuously with respect to the holder surface of the bristle holder, which enveloping surfaces are arranged substantially in a V-shape and intersect one another along a line of intersection at the location of the holder axis, the line of intersection of the two enveloping surfaces extends transversely to the longitudinal axis of the brush member, and the bristle holder is at a center position when the line of intersection and the longitudinal axis form an angle of 60° to 120°.

2. A toothbrush as claimed in claim 1, wherein the free ends of all the bristles of the bristle field are bounded by only two non-stepped enveloping surfaces which are inclined continuously with respect to the holder surface of the bristle holder.

3. A toothbrush as claimed in claim 1, wherein the two enveloping surfaces are formed by two enveloping planes.

4. A toothbrush as claimed in claim 1,
wherein, when the bristle holder is in its center position, the line of intersection of the two enveloping surfaces and the longitudinal axis of the brush member include an angle α which lies in arrange between 80° and 100°.

5. A toothbrush as claimed in claim 4, wherein the angle α has a value of 90°.

6. A toothbrush as claimed in claim 1, wherein a tangential plane to each of the two enveloping surfaces can be construed at the location of their line of intersection, and the two tangential planes include an angle β with one another, which angle lies in a range between 150° and 170°.

7. A toothbrush as claimed in claim 6, wherein the angle β has a value of 160°.

8. A brush member for a toothbrush, which brush member can be coupled detachably to a grip member of the toothbrush, which brush member has a longitudinal axis and comprises a brush holder pivotably mounted to be pivotable between a normal position and a deflection position about an axis, and at one end carries a bristle holder, which bristle holder is mounted on the brush member so as to be pivotable between a normal position and a deflection position about a holder axis which extends transversely to the longitudinal axis, and which bristle holder has a holder surface which extends substantially transversely to the holder axis and from which, in the area of the holder surface, bristles project transversely to the holder surface, which bristles together form a bristle field and are arranged around the holder axis, wherein:

the free ends of most of the bristles of the bristle field arranged around the holder axis are bounded by only two non-stepped enveloping surfaces which are inclined continuously with respect to the holder surface of the bristle holder, which enveloping surfaces are arranged substantially in a V-shape and intersect one another along a line of intersection at the location of the holder axis, the line of intersection of the two enveloping surfaces extends transversely to the longitudinal axis of the brush member, and the bristle holder is at a center position when the line of intersection and the longitudinal axis form an angle of 60° to 120°.

9. A brush member as claimed in claim 8, wherein the free ends of all the bristles of the bristle field are bounded by only two non-stepped enveloping surfaces which are inclined continuously with respect to the holder surface of the bristle holder.

10. A brush member as claimed in claim 8, wherein the two enveloping surfaces are formed by two enveloping planes.

11. A brush member as claimed in claim 8, wherein, when the bristle holder is in its center position, the line of intersection of the two enveloping surfaces and the longitudinal axis of the brush member include an angle α which lies in a range between 80° and 100°.

12. A brush member as claimed in claim 11, wherein the angle α has a value of 90°.

13. A brush member as claimed in claim 8, wherein a tangential plane to each of the two enveloping surfaces can be construed at the location of their line of intersection, and the two tangential planes include an angle β with one another, which angle lies in a range between 150° and 170°.

14. A brush member as claimed in claim 13, wherein the angle β has a value of 160°.

15. A toothbrush comprising a grip member and a brush member connected to the grip member, which brush member has a longitudinal axis and comprises a brush holder pivotably mounted to be pivotable between a normal position and a deflection position about an axis, and whose end remote from the grip member carries a bristle holder, which bristle holder is mounted on the brush member so as to be pivotable between a normal position and a deflection position about a holder axis which extends transversely to the longitudinal axis, and which bristle holder has a holder surface which extends substantially transversely to the holder axis and from which in the area of the holder surface, bristles project transversely to the holder surface, which bristles together form a bristle field and are arranged around the holder axis, wherein:

the free ends of at least a part of the bristles of the bristle field arranged around the holder axis are bounded by two non-stepped enveloping surfaces which are inclined continuously with respect to the holder surface of the bristle holder, which enveloping surfaces are arranged substantially in a V-shape and intersect one another along a line of intersection at the location of the holder axis, the line of intersection of the two enveloping surfaces extends transversely to the longitudinal axis of the brush member, the bristle holder is at a center position when the line of intersection and the longitudinal axis form an angle of 60° to 120°, brush member in addition comprises an interdental bristle holder, which is movable beyond a center position and is disposed adjacent the bristle holder substantially in the longitudinal direction of the brush member, which interdental bristle holder is mounted on the brush member so as to be movable and has a further holder surface, and from which at the location of the further holder surface interdental bristles project transversely to the further holder surface, which interdental bristles together form an interdental bristle field and are disposed at opposite sides of a central plane which extends transversely to the longitudinal axis of the brush member, the free ends of the interdental bristles being bounded by two non-stepped further enveloping surfaces which are inclined continuously with respect to the further holder surface of the interdental bristle holder, which further enveloping surfaces extend as a roof-shape with respect to the further holder surface of the interdental bristle holder and intersect one another along a further line of intersection at the location of the central plane, and the further line of intersection of the two further enveloping surfaces extends transversely to the longitudinal axis of the brush member.

16. A toothbrush as claimed in claim 15, wherein the two further enveloping surfaces are formed by two further enveloping planes.

17. A toothbrush as claimed in claim 15, wherein, when the interdental bristle holder is in its center position, the further line of intersection of the two further enveloping surfaces and the longitudinal axis of the brush member include an angle γ which lies in a range between 80° and 100°.

18. A toothbrush as claimed in claim 17 wherein the angle γ has a value of 90°.

19. A toothbrush as claimed in claim 15, wherein a further tangential plane to each of the two further enveloping surfaces can be construed at the location of the further line of intersection, and the two further tangential planes include an angle δ with one another, which angle lies in a range between 110° and 130°.

20. A toothbrush as claimed in claim 19, wherein the angle δ has a value of 120°.

21. A brush member for a toothbrush, which brush member can be coupled detachably to a grip member of the toothbrush, which brush member has a longitudinal axis and comprises a brush holder pivotably mounted to be pivotable between a normal position and a deflection position about an axis, and at one end carries a bristle holder, which bristle holder is mounted on the brush member so as to be pivotable between a normal position and a deflection position about a holder axis which extends transversely to the longitudinal axis, and which bristle holder has a holder surface which extends substantially transversely to the holder axis and from which, in the area of the holder surface, bristles project transversely to the holder surface, which bristles together form a bristle field and are arranged around the holder axis, wherein:

the free ends of at least a part of the bristles of the bristle field arranged around the holder axis are bounded by two non-stepped further enveloping surfaces which are inclined continuously with respect to the holder surface of the bristle holder, which further enveloping surfaces are arranged substantially in a V-shape and intersect one another along a line of intersection at the location of the holder axis, the line of intersection of the two enveloping surfaces extends transversely to the longitudinal axis of the brush member, the bristle holder is at a center position when the line of intersection and the longitudinal axis form an angle of 60° to 120°, the brush member also comprises an interdental bristle holder, which is movable beyond a center position and is disposed adjacent the bristle holder substantially in the longitudinal direction of the brush member, which interdental bristle holder is mounted on the brush member so as to be movable and has a further holder surface, and from which at the location of the further holder surface interdental bristles project transversely to the further holder surface, which interdental bristles together form an interdental bristle field and are disposed at opposite sides of a central plane which extends transversely to the longitudinal axis of the brush member, wherein the free ends of the interdental bristles are bounded by two non-stepped enveloping surfaces which are inclined continuously with respect to the further holder surface of the interdental bristle holder, which enveloping surfaces extend as a roof-shape with respect to the further holder surface of the interdental bristle holder and intersect one another along a further line of intersection at the location of the central plane, and the further line of intersection of the two further enveloping surfaces extends transversely to the longitudinal axis of the brush member.

22. A brush member as claimed in claim 21, wherein the two further enveloping surfaces are formed by two further enveloping planes.

23. A brush member as claimed in claim 21, wherein, when the interdental bristle holder is in its center position, the further line of intersection of the two further enveloping surfaces and the longitudinal axis of the brush member include an angle $\gamma$ which lies in a range between 80° and 100°.

24. A brush member as claimed in claim 23, wherein the angle $\gamma$ has a value of 90°.

25. A brush member as claimed in claim 21, wherein a further tangential plane to each of the two further enveloping surfaces can be construed at the location of the further line of intersection, and the two further tangential planes include an angle $\delta$ with one another, which angle lies in a range between 110° and 130°.

26. A brush member as claimed in claim 25, wherein the angle $\delta$ has a value of 120°.

* * * * *